May 28, 1968 H. SCHMIDT Plant Pat. 2,813
ALMOND TREE
Filed Feb. 2, 1967
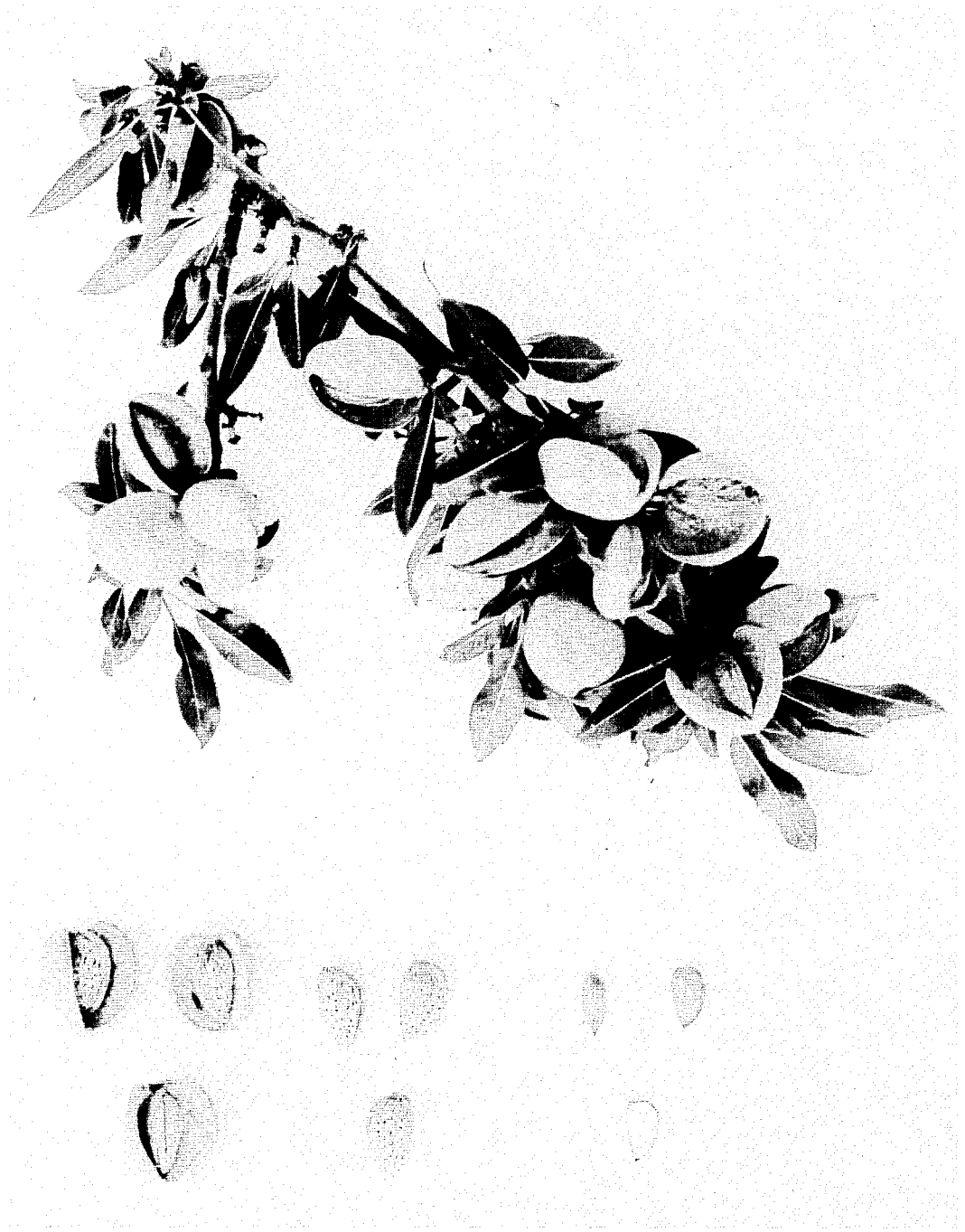
INVENTOR
Harvey Schmidt
BY
Webster & Webster
ATTORNEYS United States Patent Office Plant Pat. 2,813
Patented May 28, 1968

2,813
ALMOND TREE

Harvey Schmidt, Yuba City, Calif., assignor to George R. McFeely, Yuba City, Calif.

Filed Feb. 2, 1967, Ser. No. 613,688
1 Claim. (Cl. Plt.—30)

ABSTRACT OF THE DISCLOSURE

A new and distinct variety of almond tree which is a regular and very heavy producer of high quality nuts borne in clusters on short spurs.

*Discovery of the variety.*—The present variety of almond tree was discovered by me as an open-pollinated chance seedling growing at one edge of the almond orchard on my ranch located near Yuba City, Sutter County, Calif. After discovery of such chance seedling and recognition by me of its apparently new and distinct characteristics, I maintained the tree under careful and continuing observation and thus confirmed such characteristics.

*Asexual reproduction of the variety.*—Asexual reproduction was accomplished by budding on suitable rootstock, and this was undertaken on my behalf by a commercial nursery located near Tudor, Sutter County, Calif.; the resultant trees, of which there were a number, having been planted on my ranch located as aforesaid. These asexually reproduced trees ran true in all respects to the original tree of the variety.

*Summary of the discovery.*—The present variety of almond tree is characterized by an abundance of bloom over a relatively long period of time and with the peak bloom three or four days after the Nonpareil (unpatented); by a greater tendency to develop spurs and fruit buds on current season's growth than any other variety; and by the regular and very heavy production of commercially acceptable nuts having an above-average crack-out; i.e. a percentage of kernel to nut which is relatively high. Further, the nuts have a thin, paper, sometimes ragged, outer shell, and a smooth, hard, brittle inner shell which can be readily broken with the fingers.

The present variety of almond tree is further characterized by its compatibility with the fungus-resistant Marianna 2624 rootstock (unpatented); the latter being a desirable rootstock, but with which the Nonpareil (the most commonly grown variety) is not compatible.

The present variety of almond tree is additionally characterized—in comparison to the Nonpareil and with which it is interfertile—by more upright growth of the tree; by smaller, darker green foliage; and by a harvest period which starts five to seven days later.

*Brief description of the drawing.*—The drawing is an illustration, by photographic reproduction in color, of a twig with leaves and nuts, nuts in hull, nuts with the hull removed, and kernels, one of which is cut to expose the meat.

*Description of the variety.*—The botanical details of this new and distinct variety of almond tree—with color definitions, except those in common color terms, referenced to Maerz and Paul Dictionary of Color—are as follows:

Tree:
- *Density.*—Dense.
- *Size.*—Medium.
- *Vigor.*—Medium.

Trunk:
- *Form.*—Medium to stocky.
- *Texture.*—Medium.

Branches:
- *Form.*—Medium to stocky.
- *Texture.*—Medium.
- *Lenticels.*—Not as pronounced as Nonpareil.
- *Branching habit.*—Upright.
- *Color.*—New wood—red to green. Mature wood—brown.

Foliage: Quantity—medium.

Leaves:
- *Size.*—Shoot leaves—medium, average 2½ x ¾". Spur leaves—small, average 1½ x ¾".
- *Shape.*—Lanceolate; acutely pointed; shoot leaves tend to curl.
- *Thickness.*—Medium.
- *Texture.*—Smooth, somewhat waxy or glossy in appearance.
- *Margin.*—Crenate.
- *Petiole.*—Medium to thin.
- *Glands.*—Average number—2. Opposite. Small—inconspicuous. More or less globose; green; positioned just below leaf blade.
- *Stipules.*—None, or inconspicuous.
- *Color.*—Top side—Medium Green (23–L–5). Under side—Lighter Green (22–L–7).

Bloom:
- *Amount of bloom.*—Heavy.
- *Color.*—Pink; becomes very slight pink during expansion period.
- *Blooming period.*—In full bloom about 3 to 4 days after Nonpareil, but several days before Texas (unpatented).

Crop:
- *Bearing.*—Regular bearer.
- *Productivity.*—Very heavy.
- *Distribution of nuts on tree.*—In clusters on short spurs.
- *Harvest period.*—Starts about 4 to 5 days after Nonpareil.
- *Tenacity.*—Hangs well on tree; easy to harvest; easy to hull.

Hull:
- *Outer surface.*—Pubescent.
- *Form.*—Regular.
- *Thickness.*—Thin.
- *Flesh.*—Fleshy.
- *Suture.*—Flat, depressed.
- *Color.*—At harvest—Bistre Green (13–L–5) with a silvery sheen.
- *Dehiscence.*—Opens freely.
- *Splitting.*—Along suture.

Nut:
- *Size.*—Medium.
- *Form.*—Length/width—Ovate.
- *Shell.*—Paper; thin; ragged at times. Outer shell—hard. Inner shell—smooth; hard; brittle; readily broken with fingers.
- *Color.*—Medium Light Brown (12–I–6).
- *Pits.*—Medium to small; numerous; shallow; round.
- *Base.*—Dorsally oblique.
- *Base scar.*—Small; acute.
- *Apex.*—Acute; acuminate; prolonged at tip.
- *Wing.*—Broad; thin; extends symmetrically from tip to base.
- *Inner surface.*—Medium colored.
- *Ventral streak.*—Light; narrow; not conspicuous.
- *Percentage of kernel to nut on five-year average.*—66.60 percent.

Kernel:
- *Size.*—Medium. Average length—2.25 cm. Average width—1.24 cm. Average thickness—0.85 cm.

Kernel—Continued

*Kernels per ounce on average sample.*—20 to 25.

*Form.*—Length/width—ovate, ratio about 55%. Width/length—medium to plump, as compared to Nonpareil.

*Base.*—Square on dorsal shoulder; rounded somewhat on ventral shoulder.

*Stem scar.*—Large; rounded to somewhat oval.

*Apex.*—Acute; acuminate; prolonged at tip.

*Plumpness.*—Smooth—occasional wrinkling.

*Pellicle.*—Medium to thin.

*Pubescence.*—Smooth to lightly pubescent.

*Color.*—Medium Light Brown (13–K–8).

*Number of doubles.*—Very few.

*Defective kernels.*—None observed on average sample.

*Flavor.*—Sweet.

*Quality.*—Very good.

The tree and its nuts herein described may vary in slight detail due to climatic and soil conditions under which this variety may be grown; the present description being of the variety as grown in the Sacramento Valley of California.

I claim:

1. A new and distinct variety of almond tree, substantially as illustrated and described, which is a regular and very heavy producer of thin-shell nuts borne in clusters on short spurs; the variety being characterized—in comparison to the Nonpareil, and with which it is interfertile—by more upright growth of the tree, smaller and darker green foilage, an abundance of bloom at a peak three to four days later, a more pronounced tendency to develop spurs and fruit buds on current season's growth, a harvest period which begins five to seven days later, and generally similar nuts, but which have a substantially higher percentage of kernel to nut.

No references cited.

ROBERT E. BAGWILL, *Primary Examiner.*